United States Patent
Lee et al.

(10) Patent No.: US 8,815,288 B2
(45) Date of Patent: *Aug. 26, 2014

(54) ORAL DOSAGE FORMULATION CONTAINING BOTH IMMEDIATE-RELEASE AND SUSTAINED-RELEASE DRUGS FOR TREATING NEURODEGENERATIVE DISORDERS

(75) Inventors: Huai-Cheng Lee, Taipei (TW); Chien-Fen Chen, Taipei (TW); Chuen-Lin Din, Taipei (TW); Rong Jin Lin, Taipei (TW)

(73) Assignee: Center Laboratories, Inc., Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/063,462

(22) PCT Filed: Sep. 29, 2010

(86) PCT No.: PCT/CN2010/001519
§ 371 (c)(1),
(2), (4) Date: Mar. 10, 2011

(87) PCT Pub. No.: WO2011/038574
PCT Pub. Date: Apr. 7, 2011

(65) Prior Publication Data
US 2012/0177735 A1  Jul. 12, 2012

Related U.S. Application Data

(60) Provisional application No. 61/247,057, filed on Sep. 30, 2009.

(51) Int. Cl.
*A61K 9/44* (2006.01)
(52) U.S. Cl.
USPC .......................................................... 424/467
(58) Field of Classification Search
None
See application file for complete search history.

(56) References Cited

U.S. PATENT DOCUMENTS

| 6,682,759 | B2 | 1/2004 | Lim et al. |
| 7,255,876 | B2 | 8/2007 | Shinoda et al. |
| 2003/0144271 | A1* | 7/2003 | Shulman .................. 514/214.03 |
| 2004/0087658 | A1* | 5/2004 | Moebius ....................... 514/579 |
| 2005/0232990 | A1 | 10/2005 | Boehm et al. |
| 2009/0023778 | A1* | 1/2009 | Kimura et al. ................. 514/319 |
| 2009/0124659 | A1 | 5/2009 | Moebius |

FOREIGN PATENT DOCUMENTS

| CN | 101166543 A | 4/2008 |
| CN | 101247795 A | 8/2008 |
| JP | WO2006118265 A1 * | 11/2006 |

OTHER PUBLICATIONS

U.S. Department of Health and Human Services Food and Drug Administration CDER, Guidance for Industry Bioavailability and Bioequivalence Studies for Orally Administered Drug Products—General considerations, Mar. 2003, p. 13-14, Division of Drug Information, HFD-240 Center for Drug Evaluation and Research Food and Drug Administration, 5600 Fishers Lane, Rockville, MD 20857, USA.
U.S. Department of Health and Human Services Food and Drug Administration CDER, Guidance for Industry Dissolution Testing of Immediate Release Solid Oral Dosage Forms, Aug. 1997,p. 8-9, Office of Training and Communications Division of Communications Management The Drug Information Branch, HFD-210, 5600 Fishers Lane, Rockville, MD 20857, USA.
GlaxoSmithKline, Medication Guide PAXIL CR® (PAX-il) (paroxetine hydrochloride) Controlled-Release Tablets, Jul. 2011, p. 49, GlaxoSmithKline, Research Triangle Park, NC 27709, USA.
Valeant Pharmaceuticals North America LLC.(Manufacturer: Valeant Pharmaceuticals International, Inc.), Medication Guide Wellbutrin XL® *(WELL byu-trin) (bupropion hydrochloride extended-release tablets), Jun. 2011, p. 35, Bridgewater, NJ 08807, USA (Valeant Pharmaceuticals International, Inc. Steinbach, MB R5G 1Z7, Canada).
Sanofi-Aventis U.S. LLC, Medication Guide Ambien CR® (ām'bē-ə n see ahr) (zolpidem tartrate extended-release) Tablets C-IV, 2013, p. 26, sanofi-aventis U.S. LLC, Bridgewater, NJ 08807, USA.
Mandaltk, Effect of tablet integrity on the dissolution rate of sustained-release preparations, Jun. 21, 1996, pp. 155-157, College of Pharmacy, Xavier University of Louisiana, New Orleans 70125, USA.

* cited by examiner

*Primary Examiner* — Snigdha Maewall
(74) *Attorney, Agent, or Firm* — Chih Feng Yeh; Huntington IP Consulting Co., Ltd.

(57) ABSTRACT

Disclosed herein is an oral dosage formulation that contains both immediate-release and sustained release drugs for treating neurodegenerative disorders. The immediate-release drug in the oral dosage formulation is an acetylcholinesterase inhibitor (AChEI) with a dissolution rate of releasing more than 80% of the AChEI within 60 min; and the sustained-release drug is memantine with a dissolution rate of releasing more than 80% of memantine within 12 hours.

3 Claims, No Drawings

ORAL DOSAGE FORMULATION CONTAINING BOTH IMMEDIATE-RELEASE AND SUSTAINED-RELEASE DRUGS FOR TREATING NEURODEGENERATIVE DISORDERS

CROSS-REFERENCE TO RELATED APPLICATION

This application claims priority to PCT International Application No. PCT/CN2010/001519, filed Sep. 29, 2010, the entireties of which is incorporated herein by reference.

TECHNICAL FIELD

This disclosure in general relates to the field of pharmacology. More particularly, this disclosure relates to an oral dosage formulation that contains both immediate-release and sustained-release drugs for treating neurodegenerative disorders.

BACKGROUND ART

Description of Related Art

Neurodegenerative disorders are conditions in which cells of the brain and spinal cord are lost, which may eventually lead to central nervous system (CNS)-related dysfunction, which includes, for example, Alzheimer's disease, Parkinson's disease, Huntington's disease and etc.

Initial treatment for neurodegenerative disorders is dependent on diagnosis of the underlying condition. Currently, few therapies are available for the treatment of most neurodegenerative diseases. Therapy designed to enhance cholinergic function by inhibiting acetylcholinesterase (AChE) or by attenuating N-methyl-D-aspartate (NMDA) receptor function using 1-aminocyclohexane derivatives (e.g., memantine) has been adopted to stabilize cognitive function of the dementia patient. Recently, treatment with both 1-aminocyclohexane derivatives and acetylcholinesterase inhibitors (AChEI) have been hypothesized and demonstrated in U.S. Pat. No. 2009/0124659, which was filed by Moebius on Feb. 27, 2008. Moebius suggested that the novel combination of 1-aminocyclohexane derivatives and AChEI provides super additive effect to relieve the symptoms of dementia. The combination of drugs, are provided in one composition or in two different compositions for simultaneously or sequentially ingestion.

Current dose regimens for 1-aminocyclohexane derivatives and AChEI require patients to take more than one dose a day. This is undesirable for compliance decreases as the frequency of taking a drug increases. It also poses a difficulty for patients who start to lose cognitive function including memory to follow the dose regimens of drugs and thereby would further diminish the effects of treatment. Moreover, it is well known that certain medical conditions are most desirably treated with a dosage form that provides both immediate and extended therapeutic effects while reducing the number of doses necessary, thereby making therapy more convenient. Known examples of pharmaceutical formulations which provide both immediate and sustained-release of an active pharmaceutical ingredient may refer to U.S. Pat. No. 7,255,876 B2 to Shinoda et al. and U.S. Pat. No. 6,682,759 B2 to Lim et al. Therefore, there exists a need in this field a simple and convenient course of treatment for CNS-related dysfunction, such as dementia.

This invention address such need by providing an improved oral formulation of the two drugs proposed by Moebius (Supra), i.e., 1-aminocyclohexane derivatives and AChEI, in the improved formulation of this disclosure, one drug is designed to be released immediately upon ingestion whereas the other is designed to be released over an extended period of time. With this novel design, the course of treatment for CNS-related dysfunction such as dementia is greatly simplified by eliminating the need for a patient to take several pills either simultaneously or sequentially during the course of treatment, hence would greatly improve the effects of drugs in delaying and/or preventing the onset or progression of the disease.

SUMMARY

As embodied and broadly described herein, disclosure herein features a novel drug formulation useful for treating disorders related to central nervous system (CNS) in a subject, particularly, the human with a CNS disorder such as dementia, Alzheimer's disease, Parkinson's disease, Huntington's disease and the like.

Therefore, it is the objective of this disclosure to provide an oral dosage formulation comprising a sustained-release portion of a first compound with a dissolution rate of releasing more than 80% of the first drug within 12 hours; an immediate-release portion of a second compound with a dissolution rate of releasing more than 80% of the second compound within 60 mins; wherein the first compound is memantine, a salt, a solvate or a mixture thereof and is present in an amount of about 1-80 mg in the formulation, and the second compound is an acetylcholinesterase inhibitor (AChEI) and is present in an amount of about 1-160 mg in the formulation.

According to specific embodiments of this disclosure, the first compound is retained in a matrix, whereas the second compound is in a form of an immediate release particle or applied as a thin film deposited over the outer surface of the sustained release portion, or a single layer of a tablet constructed in two or more layers, one of the other layers of which is the sustained-release portion. According to specific examples, the oral dosage formulation may be any of a tablet, a caplet, a bi-layer tablet, a film-coated tablet or a capsule. According to certain examples, the first compound is present in an amount of about 5-60 mg, and the second compound is present in an amount of about 5-30 mg. In some example, the first compound is present in an amount of about 23-35 mg and the second compound is present in an amount of about 8-28 mg. In still some examples, the first compound is present in an amount of about 16-24 mg and the second compound is present in an amount of about 8-12 mg. In one specific example, the first compound is present in an amount of about 28 mg and the second compound is present in an amount of about 23 mg. In another specific example, the first compound is present in an amount of about 28 mg and the second compound is present in an amount of about 10 mg. In another specific example, the first compound is present in an amount of about 20 mg and the second compound is present in an amount of about 10 mg. In one specific example, the first compound is memantine. In another specific example, the first compound is memantine HCl.

According to specific embodiments of this disclosure, the second compound or AChEI useful for the described purpose is any of galantamine, tacrine, donepezil, rivastigmine, huperzine A, zanapezil, ganstigmine, phenserine, phenethylnorcymserine, cymserine, thiacymserine, SPH 1371, ER 127528, RS 1259, a salt or a solvate thereof, an enantiomer thereof, a salt or a solvate of the enantiomer or a mixture thereof. In one specific example, AChEI is donepezil. In another example, AChEI is donepezil HCl.

By combining the first compound (i.e., memantine, a salt, a solvate or a mixture thereof) in sustained-release portion and the second compound (i.e., AChEI) in an immediate-release form in a single dosage formulation, i.e., in one tablet, the course of a treatment for a subject with a CNS disorder such as dementia or Alzheimer's disease is greatly simplified for the number of tablets the subject required to take daily may be substantially reduce to a significantly low number of one or even less than one, such as half a tablet per day or 1 tablet for every two days, in accordance with some examples of this disclosure.

The details of one or more embodiments of the invention are set forth in the accompanying description below. Other features and advantages of the invention will be apparent from the detail descriptions, and from claims.

It is to be understood that both the foregoing general description and the following detailed description are by examples, and are intended to provide further explanation of the invention as claimed.

DISCLOSURE OF INVENTION

The practices of this invention are hereinafter described in detail with respect to an oral dosage formulation, particularly, an oral dosage formulation that contains both immediate-release and sustained-release drugs for treating a CNS disorder such as dementia, Alzheimer's disease, Parkinson's disease, Huntington's disease and etc.

In accordance with one embodiment of the disclosure, the oral dosage formulation comprises a sustained-release portion of a first compound with a dissolution rate of releasing more than 80% of the first compound within 12 hours; an immediate-release portion of a second compound with a dissolution rate of releasing more than 80% of the second compound within the 60 mins; wherein the first compound is memantine, a salt or, a solvate thereof, or a mixture thereof and is present in an amount of about 1-80 mg in the formulation, and the second compound is AChEI and is present in an amount of about 1-160 mg in the formulation.

The term "salt" refers herein as a salt which is formed by the interaction of a base (such as memantine or donepezil in this disclosure) with an acid, including organic or inorganic types of acids such as hydrochloric acid, hydrobromic acid, hydroiodic acid, perchloric acid, methylsulfonic acid, sulfuric acid, nitric acid, phosphoric acid, acetic acid, propionic acid, glycolic acid, pyruvic acid, malonic acid, succinic acid, maleic acid, fumaric acid, tartaric acid, cirtic acid, benzoic acid, carbonic acid, cinnamic acid, methanesulfonic acid, ethanesulfonic acid, hydroxyehtanesulfonic acid, benzenesulfonic acid, p-toluene sulfonic acid, cyclohexanesulfamic acid, salicyclic acid, p-aminosalicyclic acid, 2-phenoxybenzoic acid and 2-acetoxybenzoic acid. In one preferred example, the salt is memantine hydrochloride. In another example, the salt is donepezil hydrochloride. The term "solvate" herein refers to a complex formed by the interaction of a compound (such as memantine or donepezil in this disclosure) with surrounding solvent molecules, such as water, ethanol, and etc. In one example, the solvate of a first compound is a memantine hydrate.

The term "acetylcholinesterase inhibitor" or "AChEI" refers herein to a drug that enhances the functions of cholinergic neurons by inhibiting the activity of acetylcholinesterase (AChE). AChEI useful for the described purpose is any of galantamine, tacrine, donepezil, rivastigmine, huperzine A, zanapezil, ganstigmine, phenserine, phenethylnorcymserine, cymserine, thiacymserine, SPH 1371, ER 127528, RS 1259, a salt or a solvate thereof, an enantiomer thereof, a salt or a solvate of the enantiomer or a mixture thereof. Suitable salts of AChEI may be formed by the interaction of any AChEI compound with an acid, such as the acids described above. In one specific example, AChEI is donepezil hydrochloride((R,S)-1-benzyl-4-[(5,6-dimethoxy-1-indanone)-2-yl]-methyl-piperidine hydrochloride).

The term "sustained-release" herein refers to the release of the therapeutic compound occurs over an extended period of time leading to lower peak plasma concentrations and/or is directed to a prolonged $T_{max}$ as compared to "immediate-release". The sustained-release portion of the dosage formulation is designed to deliver memantine, a salt or a solvate thereof to the digestive system of a subject continuously over a period of time for at least an hour and preferably more than several hours. The dissolution rate is slow enough that at least about 60% of memantine, a salt or a solvate thereof remains unreleased after two hours and more preferably at least about 70% of memantine, a salt or a solvate thereof remains unreleased after two hours. In general, the memantine, a salt or a solvate thereof will be at least 80% released within 12 hours, and will be at least 90% released within 24 hours. The memantine, a salt or a solvate thereof in the sustained-release portion of the formulation is retained in a matrix that is composed by at least one polymer that includes, but is not limited to, methylcellulose (MC), ethyl cellulose (EC), hydroxypropyl cellulose (HPC), hydroxypropyl methylcellulose (HPMC), carboxyl methylcellulose (CMC), microcrystalline cellulose, cellulose acetate, cellulose propionate, cellulose acetate propionate, cellulose acetate butyrate, cellulose acetate phthalate, cellulose triacetate, polymethyl methacrylate, polyethyl methacrylate, polyethylene glycol, polyvinyl alcohol, polyvinyl acetate, polyvinyl alcohol-ethylene glycol, carbomer and a combination thereof. Suitable polymer(s) for producing the matrix are those sold under the trademark that includes, but is not limited to, CELPHERE® CP708, EUDRAGIT®, OPADRY®, ACRYL-EZE®, SURELEASE®, METHOCEL®, ETHOCEL®, or SURETERIC®.

The term "$T_{max}$" as used herein means the time to reach maximum plasma concentration of the active compound or drug (e.g., memantine or AchEl) achieved by the ingestion of the composition of this invention.

The sustained-release portion may be prepared by mixing memantine, a salt, a solvate or a mixture thereof with the matrixpolymer described above and suitable binders, then directly compressing the mixture into tablets. Alternatively, the sustained-release portion may contain sustained-release fine particles or pellets that are produced by any known method such as wet granulation or dry granulation method. In one example, the sustained-release fine particles or pellets are produced by wet granulation, particularly, fluid bed granulation. Wet granulation generally involves the steps of mixing the drug, the matrix polymer as described above, a diluent and a binder solution, drying the moist granules, and screening through a suitable sieve to produce particles with desired sizes. Useful binders include, but are not limited to, acacia, tragacanth, alginic acid, sodium alginate, carbomer, carboxymethylcellulose sodium, carrageenan, cellulose acetate phthalate, ceratonia, copovidone, dextrates, dextrin, dextrose, methylcellulose, ethylcellulose, carboxymethyl cellulose, hydroxypropyl methyl cellulose, hydroxyethyl cellulose; hydroxyethylmethyl cellulose; hydroxypropyl cellulose; hydroxypropyl starch; hypromellose, gelatin, starch, sucrose, lactose, magnesium aluminum silicate, maltodextrin, maltose, microcrystalline cellulose, polyvinyl pyrrolidone, polyacrylamide, povidone and pregelatinized starch. Useful diluents include, but are not limited to, ammonium alginate, calcium carbonate, calcium phosphate dibasic, calcium phosphate tribasic, calcium sulfate, cellulose, cellulose acetate, compressible sugar, dextrates, dextrin, dextrose, erythritol; ethylcellulose, fructose, fumaric acid, glyceryl palmitostearate, lactitol, lactose, mannitol, magnesium carbonate, magnesium oxide, maltodextrin, maltose, microcrystalline cellulose, polydextrose, polymethacrylates, sodium chloride, sorbitol, starch, sucrose, sugar spheres, ARBOCEL A300®; LUDIPRESS®; and SUPER TAB®. In certain examples, the sustained-release portion is prepared by mixing memantine, a salt, a solvate or a mixture thereof with a sugar sphere made of microcrystalline cellulose (e.g., CELPHERE® CP708), and at least one other matrix polymer as described above, to form memantine containing granules or pellets. Then, each of the memantine containing pellets is coated with a sustained-release film containing at least a matrix polymer described above (e.g., EUDRAGIT®), a diluent (e.g., talc) and a stabilizer (e.g., triethyl citrate) to produce the sustained-release portion or the SR portion. Optionally, the SR portion may be further coated with a protective coating to delay the release of the active ingredient therein. The protective coating may comprise at least one of the matrix polymer as described above. In one example, the protective coating comprises hydroxymethyl cellulose and polyethylene glycol. In another example, the protective coating comprises triethyl citrate (TEC) and talc. The SR coating and the protective coating may be applied as a film respectivley depositied over the sustained-release pellets and the sustained-release portion, by any known techniques such as spraying, dipping, or pan-coating.

The immediate-release portion of the dosage formulation is designed to rapidly disintegrate upon contacting a fluid such as water and allow fast leaching out of AChEI to the environment continuously over a short period of time, such as several minutes or in an hour. The dissolution rate is fast enough that at least 80% of AChEI is released within the first 60 mins. In general, at least 90% of AChEI will be released within 2 hours. The AChEI in the immediate-release portion is in a form of an immediate-release particle or applied as a thin film deposited over the outer surface of the sustained release portion, or a single layer of a tablet constructed in two or more layers, one of the other layers of which is the sustained-release portion. The immediate-release particles may be produced by any known method, such as dry or wet granulation method as described above. In one example, AChEI is mixed with disintegrants and/or binders, and adsorbents and then the mixture is subjected to either fluid bed granulation or spray drying to produce particles with desired immediate-release property. Examples of disintegrants include, but are not limited to, cross-linked polyvinyl pyrrolidone or crospovidone, starch derivatives such as carboxy methyl cellulose and cellulose derivatives; calcium alginate; carboxymethylcellulose calcium; carboxymethylcellulose sodium; croscarmellose sodium; docusate sodium; hydroxypropyl cellulose; magnesium aluminum silicate; methylcellulose; polacrilin potassium; sodium alginate; sodium starch glycolate and pregelatinized starch. Examples of adsorbents include, but are not limited to, aluminum hydroxide adjuvant; aluminum oxide; aluminum phosphate adjuvant; attapulgite; bentonite; powdered cellulose; colloidal silicon dioxide; hectorite; kaolin; magnesium aluminum silicate; magnesium carbonate; microcrystalline cellulose; pectin; polycarbophil; and saponite. At least 50% of the immediate-release particles thus prepared have a size that may pass 80 mesh; preferably, 60 mesh; more preferably, 40 mesh; and most preferably, 20 mesh.

According to specific embodiments, the sustained-release portion and the immediate-release portion respectively prepared by steps as described above are combined with glidants and lubricants to form the oral dosage formulation of this disclosure. Suitable glidants include, but are not limited to, calcium phosphate, tribasic; calcium silicate; cellulose, powdered; colloidal silicon dioxide; magnesium silicate; magnesium trisilicate; silicon dioxide; starch and talc. Suitable lubricants include, but are not limited to, calcium stearate; glyceryl behenate; glyceryl palmitostearate; magnesium lauryl sulfate; magnesium stearate; polyethylene glycol; potassium benzoate; sodium lauryl sulfate; sodium stearyl fumarate; stearic acid; talc and zinc stearate. The oral dosage formulation of this disclosure may be in a form of tablets, caplets, bi-layer tablets, film-coated tablets, pills, capsules or the like. Tablets in accordance with this disclosure can be prepared by any mixing and tabletting techniques that are well known in the pharmaceutical formulation industry. In some examples, the dosage formulation is fabricated by direct compressing the respectively prepared sustained-release portion and the immediate-release portion by punches and dies fitted to a rotary tabletting press, ejection or compression molding or granulation followed by compression. In one example, the dosage form is a single layer tablet containing therein both the sustained-release and the immediate-release portions. In another example, the dosage form is a tablet containing two layers, with one layer being the immediate-release portion and the other layer being the sustained-release portion. In still another example, the dosage form is a film-coated tablet having a sustained-release portion and a thin film of the immediate-release portion deposited over the outer surface of the sustained-release portion. The immediate-release portion may be applied as a coating over the sustained-release portion by any known techniques such as spraying, dipping, or pan-coating, or as an additional layer by tabletting or compressing in the same manner as the sustained-release portion. In some examples, the tablet is a scoring tablet having a score line at the center of the tablet for breaking the tablet into two equal halves when necessary. In other examples, the oral dosage formulation is in a form of capsule containing therein both the sustained-release particles or pellets of the first compound (i.e., memantine, a salt, a solvate, or a mixture thereof) and the immediate-release particles or pellets of the second compound (i.e., AChEI, a salt or a solvate thereof, an enantiomer thereof, a salt or a solvate of the enantiomer or a mixture thereof).

Specific examples of the oral dosage formulation of this disclosure include about 1-80 mg of memantine, a salt, a solvate or a mixture thereof, such as 5-60 mg, 23-35 mg or 16-24 mg of memantine, a solvate or a mixture thereof; and about 1-160 mg of AChEI, a salt or a solvate thereof, an enantiomer thereof, a salt or a solvate of the enantiomer or a mixture thereof, such as 5-30 mg, 8-28 mg or 8-12 mg of AChEI, a salt or a solvate thereof, an enantiomer thereof, a salt or a solvate of the enantiomer or a mixture thereof. In one example, memantine, a solvate or a mixture thereof is present in an amount of about 28 mg/dosage formulation, and AChEI, a salt or a solvate thereof, an enantiomer thereof, a salt or a solvate of the enantiomer or a mixture thereof is present in an amount of about 23 mg/dosage formulation. In another example, memantine, a salt, a solvate or a mixture thereof is present in an amount of about 28 mg/dosage formulation, and AChEI, a salt or a solvate thereof, an enantiomer thereof, a salt or a solvate of the enantiomer or a mixture thereof is present in an amount of about 10 mg/dosage formulation. In still another example, memantine, a salt, a solvate or a mixture thereof is present in an amount of about 20 mg/dosage formulation, and AChEI, a salt or a solvate thereof, an enantiomer thereof, a salt or a solvate of the enantiomer or a mixture thereof is present in an amount of about 10 mg/dosage formulation.

It must be noted that as used herein and in the appended claims, the singular forms "a", "an", and "the" include plural referents unless the context clearly dictates otherwise.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. As used herein, the term "about" generally means within 10%, 5%, 1%, or 0.5% of a given value or range. Alternatively, the term "about" means within an acceptable standard error of the mean, when considered by one of ordinary skill in the art dictates otherwise. Except for particular values described in the examples, or unless otherwise stated, when referring to a specified weight, a period of time, temperature, operating condition, amount and etc, the particular value is modified with the term "about." Thus, unless otherwise indicated, where particular values are described in the application and claims, the particular value is an approximation and may vary according to various needs.

Unless defined otherwise, all technical and scientific terms used herein have the same meaning as commonly understood by one of ordinary skill in the art to which this invention belongs. Although any methods and materials similar or equivalent to those described herein can also be used in the practice of the present invention, exemplary methods and materials are described for illustrative purposes.

The following Examples are provided to illustrate certain aspects of the present invention and to aid those of skilled in the art in practicing this invention. These Examples are in no way to be considered to limit the scope of the invention in any manner.

EXAMPLES

Example 1

Production of IR/SR Tablets and In Vitro Dissolution Performance of the Produced Tablets In this example, the sustained-release (SR) portion and the immediate-release (IR) portion were separately produced in accordance with steps and conditions described in examples 1.1 and 1.2. The tablet containing both the IR and SR portions (or the IR/SR Ttablet), was subsequently made by comprising the IR and SR portions together in accordance with the conditions set in Example 1.3.

1.1 Production of SR Portion

In operation, the SR portion was produced by forming a memantine pellet first; then followed by coating the thus made memantine pellet with a sustained release film (i.e., SR film) outside each pellet. The memantine pellet was produced by mixing the CELPHERE spherical seed core, memantine, HPMC and PEG 400 listed in the SR pellet formulation in Table 1 in a fluid bed machine under processing parameters set as follows:

| Processing Parameters for Forming Memantine Pellet | |
|---|---|
| Temperature | 45° C. |
| Air Pressure | 0.45 bar |
| Atomizing air | 1.00 bar |
| Flow speed | 26 rpm (6 g/min) |
| Pellet temperature | 28.5° C. |

Each of the thus prepared memantine pellets were then coated with a sustained-release film in accordance with the SR-coating formulation listed in Table 1 under processing parameters set as follows:

| Processing Parameters for Forming SR-Film Coated Memantine Pellet | |
|---|---|
| temperature | 40° C. |
| Air Pressure | 0.45 bar |
| Atomizing air | 1.00 bar |
| Flow speed | 18 rpm (4.5 g/min) |
| Pellet temperature | 27.5° C. |

1.2 Production of IR Portion

The IR portion was prepared in accordance with the IR granule formulation listed in Table 1 and steps as described below. Briefly, donepezil and microcrystalline cellulose (i.e., MCC PH101) were mixed in equal amount to form a mixture that passed 80 mesh. Then, the remaining microcrystalline cellulose, other excipients including lactose and povidone (i.e., PVK30) were added thereto, followed by the addition of water to form wet granule that passed 20 mesh. The granules were subsequently dried at 50° C. for 3 hours.

1.3 Production of IR/SR Tablet Formulation

PVPPXL-10 and the SR portion of example 1.1 were added to the dry granules of example 1.2 and mixed at a speed at 22 rpm for 10 min. Then, magnesium stearate (i.e., a lubricant) was added, and the resulted mixture was subsequently compressed into tablets and thereby produced IR/SR tablets having a hardness of 6 Kg, 8 Kg and 10 kg, respectively; and a weight of about 350 mg.

TABLE 1

Unit dose composition of IR/SR Tablet, 350 mg Tablet

| Ingredients | Weight, mg |
|---|---|
| SR Pellet Formulation | |
| CELPHERE ® CP708[a] | 110 |
| memantine | 28 |
| HPMC | 8.0 |
| PEG 400 | 0.8 |
| Subtotal | 146.8 |
| SR-Coating Formulation | |
| Eudraigit RS 30D[b] | 26.4 |
| Talc | 13.2 |
| TEC | 5.3 |
| Total | 191.7 |
| IR Granule Formulation | |
| Donepezil | 10 |
| MCC PH101 | 66 |
| Lactose | 30 |
| PVP K30 | 10 |
| Total | 116 |
| IR/SR Tablet Formulation | |

TABLE 1-continued

Unit dose composition of IR/SR Tablet, 350 mg Tablet

| Ingredients | Weight, mg |
|---|---|
| SR Portion | 192 |
| IR Portion | 116 |
| PVPP XL-10 | 40 |
| Magnesium Stearate | 2 |
| Total | 350 |

[a]CELPHERE ®CP708 (700-800 μm) was purchased from Asahi Kasei Chemicals Corporation, (Tokyo, Japan)
[b]Eudraigit RS 30D was purchased from Evonik Röhm GmbH (Darmstadt, Germany).
HPMC = hydroxypropyl methyl cellulose
PEG 400 = polyethylene glycol 400
TEC = triethyl citrate
MCC PH101 = microcrystalline cellulose
PVPP XL-10 = polyvinyl polypyrrolidone, Copovidone
PVP K 30 = polyvinyl pyrrolidone, Povidone 1.4 In Vitro Dissolution Performance of the IR/SR Tablet of Example 1.3

The in vitro dissolution profile of the IR/SR tablet of Example 1.3 was obtained under simulated gastric condition. The dissolution tests were performed in 0.1 N HCl-pH 1.2 solution at a temperature of 37° C. Samples of dissolution media were collected at predetermined intervals and analyzed by high performance liquid chromatography (HPLC). The dissolution profiles of memantine and donepezil obtained from HPLC analysis are provided in Tables 2 and 3, respectively.

TABLE 2

In Vitro Dissolution Profile of Memantine from IR/SR Tablet of Example 1.3 in 0.1N HCl

| | | | | Tablet compression pressure | | | | | |
|---|---|---|---|---|---|---|---|---|---|
| | | SR coating | | 6 kg | | 8 kg | | 10 kg | |
| Media | T, h | Mean Diss, % | SD | Mean Diss, % | SD | Mean Diss, % | SD | Mean Diss, % | SD |
| 0.1N HCl | 0 | 0 | 0 | 0 | 0 | 0 | 0 | 0 | 0 |
| | 1 | 10.2 | 2.53 | 14.8 | 0.67 | 12.2 | 1.02 | 11.3 | 1.08 |
| | 2 | 13.2 | 0.00 | 27.4 | 2.19 | 25.1 | 1.57 | 22.3 | 0.70 |
| | 4 | 26.5 | 3.26 | 66.1 | 2.90 | 60.4 | 0.54 | 56.2 | 1.48 |
| | 6 | 71.2 | 3.12 | 113.4 | 0.50 | 101.1 | 1.31 | 93.3 | 0.14 |
| | 8 | 109.9 | 0.73 | 130.0 | 5.37 | 120.3 | 4.70 | 109.4 | 3.49 |
| | 12 | 113.9 | 1.58 | 130.4 | 5.97 | 118.1 | 0.81 | 106.7 | 4.43 |

TABLE 3

In Vitro Dissolution Profile of Donepezil from IR/SR Tablet of Exmple 1.3 in 0.1N HCl

| | Tablet compression pressure | | | | | |
|---|---|---|---|---|---|---|
| | 6 kg | | 8 kg | | 10 kg | |
| T' Min | Mean Diss, % | SD | Mean Diss, % | SD | Mean Diss, % | SD |
| 0 | 0.0 | 0.0 | 0.0 | 0.0 | 0.0 | 0.0 |
| 45 | 72.5 | 1.1 | 76.8 | 0.4 | 81.5 | 5.1 |
| 60 | 74.1 | 0.6 | 77.9 | 1.1 | 83.4 | 3.0 |
| 120 | 73.1 | 0.8 | 76.4 | 0.1 | 81.7 | 2.2 |

The results indicated that for the SR portion, at least about 70% of memantine remained un-released (i.e., remained in the SR coating) after contacting simulated gastric condition for 2 hours, and over 90% of memantine were released after 6 hours for all tablets that were produced, i.e., tablets having a hardness of 6, 8 and 10 Kg, respectively. As to IR portion, only tablets having a hardness of 10 Kg satisfied the requirement that over 80% of donepezil were released within an hour after contacting the simulated gastric condition.

Example 2

Production of IR/SR Scoring Tablets and In Vitro Dissolution Performance of the Produced Tablets 2.1 Production of IR/SR Scoring Tablet Formulation IR/SR tablets with or without scoring marks were produced in accordance with the unit dose formulation listed in Table 4 and according to steps and similar process conditions as described in Example 1, and tablets having a hardness of 5 Kg and an average weight of 350 mg were produced.

TABLE 4

Unit dose composition of IR/SR Tablet, 350 mg Tablet

| Ingredients | Weight, mg |
|---|---|
| SR Pellet Formulation | |
| CELPHERE ® CP708[a] | 73.4 |
| memantine | 20 |
| HPMC | 6.0 |
| PEG 400 | 0.6 |
| Subtotal | 100 |
| SR-Coating Formulation | |
| Eudraigit RS 30D[b] | 22 |
| Plasacryl T120 | 0.2 |
| TEC | 4.4 |
| Total | 126.6 |
| IR Granule Formulation | |
| Donepezil | 10 |
| MCC KG802 | 56 |
| PC-10 | 15 |
| Sugar spheres | 62 |
| PVP K30 | 5 |
| Total | 148 |
| IR/SR Tablet Formulation | |
| SR Portion | 128 |
| IR Portion | 148 |

TABLE 4-continued

Unit dose composition of IR/SR Tablet, 350 mg Tablet

| Ingredients | Weight, mg |
|---|---|
| Cushioning pellets | 52 |
| PVPP XL-10 | 20 |
| Magnesium Stearate | 2 |
| Total | 350 |

[a]CELPHERE ®CP708 (700-800 μm) was purchased from Asahi Kasei Chemicals Corporation, (Tokyo, Japan)
[b]Eudraigit RS 30D was purchased from Evonik Röhm GmbH (Darmstadt, Germany).
Plasacryl T120 = an aqueous emulsion of glyceryl monostearate and triethyl citrate
HPMC = hydroxypropyl methyl cellulose
PEG 400 = polyethylene glycol 400
TEC = triethyl citrate
MCC KG802 = microcrystalline cellulose
PC-10 = pre-gelatinized starch
PVPP XL-10 = polyvinyl polypyrrolidone, Copovidone
PVP K 30 = polyvinyl pyrrolidone, Povidone 2.2 In Vitro Dissolution Performance of the IR/SR Tablets of Example 2.1

The IR/SR tablets of Example 2.1 (with or without scoring marks) having a weight gain of 22% (i.e., the percentage of weight increased for the sustained-release portion after inclusion of the SR coating around the SR pellet) were used in this example. The dissolution tests were performed in accordance with steps as described in Example 1.4. The dissolution profiles of memantine and donepezil obtained from HPLC analysis are provided in Tables 5 and 6, respectively.

TABLE 5

In Vitro Dissolution Profile of Memantine from IR/SR Tablets of Exmple 2.1 in 0.1N HCl

| Media | Time (hr) | Non-scoring Tablets | | Scoring Tablets | |
|---|---|---|---|---|---|
| | | Mean Diss, (%) | SD | Mean Diss, (%) | SD |
| 0.1N HCl | 0 | 0 | 0 | 0 | 0 |
| | 1 | 17.1 | 0.43 | 19.8 | 3.26 |
| | 2 | 32.6 | 1.18 | 30.5 | 1.50 |
| | 3 | 51.7 | 1.41 | 49.8 | 6.33 |
| | 4 | 67.8 | 4.26 | 62.3 | 1.61 |
| | 6 | 93.2 | 7.41 | 87.8 | 3.79 |
| | 8 | 98.9 | 5.81 | 92.6 | 3.03 |
| | 12 | 100.3 | 7.55 | 97.4 | 1.90 |

TABLE 6

In Vitro Dissolution Profile of Donepezil from IR/SR Tablet of Exmple 2.1 in 0.1N HCl

| Media | Time (hr) | Non-scoring Tablets | | Scoring Tablets | |
|---|---|---|---|---|---|
| | | Mean Diss, (%) | SD | Mean Diss, (%) | SD |
| 0.1N HCl | 0 | 0 | 0 | 0 | 0 |
| | 10 | 69.1 | 10.5 | 73.3 | 3.3 |
| | 30 | 77.8 | 5.2 | 84.1 | 4.4 |
| | 45 | 80.4 | 7.1 | 86.6 | 3.6 |
| | 60 | 84.7 | 7.9 | 90.7 | 4.3 |
| | 120 | 88.8 | 5.9 | 93.6 | 4.1 |

The results indicated that for the SR portion, at least about 60% of memantine remained un-released (i.e., remained in the SR coating) after contacting simulated gastric condition for 2 hours, and about 90% of memantine were released after 6 hours for all tablets that were produced. As to IR portion, over 80% of donepezil was released within an hour after contacting the simulated gastric condition. Further, scoring marks have negligible effects on the dissolution of either memantine or donepezil.

Example 3

Production of IR/SR Tablets Having Protective Coatings to the SR Portion and In Vitro Dissolution Performance of the Produced Tablets In this example, an extra layer of protective coating was applied to the SR portion, and the SR portion having a protective coating was then used for the production of each IR/SR tablet, in accordance with the indicated formulation in Table 7.

3.1 Production of IR/SR Scoring Tablet Formulation

IR/SR tablets with or without protective coatings were produced in accordance with the unit dose formulation listed in Table 7 and according to steps and similar process conditions described in Example 1, and tablets having a hardness of 5 Kg and an average weight of 360 mg were produced. Process parameters for forming Memantine pellets were as described in Example 1.1; process parameters for forming memantine pellets having SR-films and/or protective films coated thereon are as follows.

| Processing Parameters for Forming SR-Film Coated Memantine Pellet | |
|---|---|
| temperature | 30° C. |
| Air Pressure | 0.48 bar |
| Atomizing air | 1.20 bar |
| Flow speed | 14 rpm (4.0 g/min) |
| Pellet temperature | 22° C. |
| Processing Parameters for Forming Protective Film Coated Memantine Pellet | |
| temperature | 30° C. |
| Air Pressure | 0.48 bar |
| Atomizing air | 1.20 bar |
| Flow speed | 14 rpm (4.0 g/min) |
| Pellet temperature | 24° C. |

TABLE 7

Unit dose composition of IR/SR Tablet, 360 mg Tablet

| Ingredients | Weight, mg |
|---|---|
| SR Pellet Formulation | |
| CELPHERE ® CP305[a] | 100 |
| memantine | 20 |
| HPMC | 6.0 |
| PEG 400 | 0.6 |
| Subtotal | 126.6 |
| SR-Coating Formulation | |
| Eudraigit NE 30D[b] | 31.7 |
| Talc | 31.7 |
| HPMC | 0.8 |
| Subtotal | 190.7 |
| Protective Coating Formulation | |
| Eudraigit E-100[b] | 9.5 |
| TEC | 1.0 |
| Talc | 4.8 |
| Total | 205.9 |
| IR Granule Formulation | |

TABLE 7-continued

Unit dose composition of IR/SR Tablet, 360 mg Tablet

| | | |
|---|---|---|
| Donepezil | | 10 |
| MCC KG802 | | 125 |
| PC-10 | | 15 |
| Total | | 150 |

IR/SR Tablet Formulation

| | Weight, mg | |
|---|---|---|
| Ingredients | w/o Protective Coating | With Protective Coating |
| SR Portion | 190 | 205 |
| IR Portion | 150 | 140 |
| PVPP XL-10 | 10 | 10 |
| Magnesium Stearate | 2 | 2 |
| Total | 352 | 357 |

<sup>a</sup>CELPHERE ®CP305 (300-500 μm) was purchased from Asahi Kasei Chemicals Corporation, (Tokyo, Japan)
<sup>b</sup>Eudraigit NE 30D and Eudraigit E-100 were purchased from Evonik Röhm GmbH (Darmstadt, Germany).
HPMC = hydroxypropyl methyl cellulose
PEG 400 = polyethylene glycol 400
TEC = triethyl citrate
MCC KG802 = microcrystalline cellulose
PC-10 = pre-gelatinized starch
PVPP XL-10 = polyvinyl polypyrrolidone, Copovidone
PVP K 30 = polyvinyl pyrrolidone, Povidone 3.2 In Vitro Dissolution Performance of the IR/SR Tablets of Example 3.1

The IR/SR tablets of Example 3.1 (with or without protective coating outside the SR portion) having a weight gain of 25% (i.e., the percentage of weight increased for the sustained-release portion after inclusion of the SR coating around the SR pellet) were used in this example. The dissolution tests were performed in accordance with steps described in Example 1.4. The dissolution profiles of memantine obtained from HPLC analysis are provided in Table 8.

TABLE 8

In Vitro Dissolution Profile of Memantine from IR/SR Tablets of Exmple 3.1 in 0.1N HCl

| | | w/o Protective Coating | | With Protective Coating | |
|---|---|---|---|---|---|
| Media | Time (hr) | Mean Diss, (%) | SD | Mean Diss, (%) | SD |
| 0.1N HCl | 0 | 0 | 0 | 0 | 0 |
| | 1 | 16.4 | 2.63 | 20.9 | 1.31 |
| | 2 | 34.1 | 1.73 | 32.9 | 0.25 |
| | 3 | 53.6 | 7.66 | 49.4 | 4.83 |
| | 4 | 66.1 | 7.52 | 61.2 | 1.16 |
| | 6 | 88.3 | 1.31 | 81.6 | 2.68 |
| | 8 | 93.2 | 3.56 | 100.9 | 1.85 |
| | 12 | 100.7 | 13.66 | 119.8 | 3.57 |

The results indicated that by protecting the SR portion with an additional layer of matrix polymer outside the SR film, may delay the release of memantine only slightly. With or without the additional layer of protection, at least about 60% of memantine remained un-released after contacting simulated gastric condition for 2 hours, and at least about 80% of memantine were released after 6 hours for all tablets that were produced.

Other Embodiments

All of the features disclosed in this specification may be combined in any combination. Each feature disclosed in this specification may be replaced by an alternative feature serving the same, equivalent, or similar purpose. For example, both the first and second compounds may both exist as sustained-release particles in the dosage formulation. In one embodiment, the dosage formulation may include two components, wherein each component contains both sustained-release and immediate-release particles of one active compound. For example, the dosage formulation may comprise a first component comprising both the sustained-release and immediate-release particles of the first compound; and a second component comprising both the sustained-release and immediate-release particles of the second compound. In another example, the first component may contain both the sustained-release and immediate-release particles of the first compound; whereas the second component may comprise only the immediate-release particles of the second compound or the sustained-release particles of the second compound. In another variation, the first component may contain either the immediate-release particles or the sustained-release particles of the first compound; whereas the second component may contain both the immediate-release particles and the sustained release particles of the second compound. Thus, unless expressly stated otherwise, each feature disclosed is only an example of a generic series of equivalent or similar features. From the above description, one skilled in the art can easily ascertain the essential characteristics of the present invention, and without departing from the spirit and scope thereof, can make various changes and modifications of the invention to adapt it to various usages and conditions. Thus, other embodiments are also within the scope of the following claims.

What is claimed is:

1. An oral dosage formulation for treating a disorder related to central nervous system (CNS), consists of ingredients set forth bellow,

| Ingredients | Weight, mg |
|---|---|
| Sustained Release (SR) Pellet Formulation | |
| Microcrystalline cellulose | 100 |
| memantine | 20 |
| hydroxypropyl methyl cellulose | 6.0 |
| Polyethylene glycol | 0.6 |
| Subtotal | 126.6 |
| SR-Coating Formulation | |
| Polymethyl methacrylate | 31.7 |
| Talc | 31.7 |
| hydroxypropyl methyl cellulose | 0.8 |
| Subtotal | 190.7 |
| Protective Coating Formulation | |
| Polymethyl methacrylate | 9.5 |
| triethyl citrate | 1.0 |
| Talc | 4.8 |
| Total | 205.9 |
| Immediate Release (IR) Granule Formulation | |
| Donepezil | 10 |
| microcrystalline cellulose | 125 |
| pre-gelatinized starch | 15 |
| Total | 150 |

-continued

| Ingredients | Weight, mg | |
|---|---|---|
| IR/SR Tablet Formulation | | |
| | without Protective Coating | With Protective Coating |
| SR-Pellet/SR-Coating | 190 | 205 |
| IR Granule | 150 | 140 |
| polyvinyl polypyrrolidone | 10 | 10 |
| Magnesium Stearate | 2 | 2 |
| Total | 352 | 357. |

2. The oral dosage formulation of claim 1, wherein the tablet is scoring tablet having a score line at the center of the tablet for breaking the tablet into two equal parts.

3. The oral dosage formulation of claim 1, wherein the disorder related to central nervous system (CNS) is Alzheimer's disease.

* * * * *